(12) United States Patent
Zinger et al.

(10) Patent No.: US 8,021,325 B2
(45) Date of Patent: Sep. 20, 2011

(54) LIQUID DRUG MEDICAL DEVICE

(75) Inventors: Freddy Zinger, Ra'anana (IL); Igor Denenburg, Rehovot (IL)

(73) Assignee: Medimop Medical Projects Ltd., Ra'anana (IL)

( * ) Notice: Subject to any disclaimer, the term of this patent is extended or adjusted under 35 U.S.C. 154(b) by 1132 days.

(21) Appl. No.: 11/568,421

(22) PCT Filed: Apr. 6, 2005

(86) PCT No.: PCT/IL2005/000376
§ 371 (c)(1),
(2), (4) Date: Oct. 27, 2006

(87) PCT Pub. No.: WO2005/105014
PCT Pub. Date: Nov. 10, 2005

(65) Prior Publication Data
US 2008/0009789 A1    Jan. 10, 2008

Related U.S. Application Data

(60) Provisional application No. 60/587,550, filed on Jul. 14, 2004, provisional application No. 60/589,568, filed on Jul. 21, 2004.

(30) Foreign Application Priority Data

Apr. 29, 2004 (IL) .......................................... 161660

(51) Int. Cl.
*A61M 37/00* (2006.01)
(52) U.S. Cl. ....................................................... 604/89
(58) Field of Classification Search .................... 604/89, 604/82, 91
See application file for complete search history.

(56) References Cited

U.S. PATENT DOCUMENTS

| | | | |
|---|---|---|---|
| 62,333 | A | 2/1867 | Holl |
| 1,704,817 | A | 3/1929 | Ayers |
| 1,930,944 | A | 10/1933 | Schmitz, Jr. |
| 2,326,490 | A | 8/1943 | Perelson |
| 2,931,668 | A | 4/1960 | Baley |
| 2,968,497 | A | 1/1961 | Treleman |
| 3,059,643 | A | 10/1962 | Barton |
| D198,499 | S | 6/1964 | Harautuneian |
| 3,484,849 | A | 12/1969 | Huebner et al. |
| 3,618,637 | A | 11/1971 | Santomieri |
| 3,757,981 | A | 9/1973 | Harris, Sr. et al. |
| 3,826,261 | A | 7/1974 | Killinger |
| 3,885,607 | A | 5/1975 | Peltier |
| 3,957,052 | A | 5/1976 | Topham |

(Continued)

FOREIGN PATENT DOCUMENTS

DE    1913926 A1    9/1970

(Continued)

OTHER PUBLICATIONS

Office Action issued Nov. 12, 2010 in U.S. Appl. No. 29/334,697.

(Continued)

*Primary Examiner* — Nicholas D Lucchesi
*Assistant Examiner* — Weng Lee
(74) *Attorney, Agent, or Firm* — Panitch Schwarze Belisario & Nadel LLP

(57) ABSTRACT

The present invention relates to liquid drug medical devices for enabling the administration of liquid drugs, and also a needle shield removal device for safely removing needle shields.

7 Claims, 12 Drawing Sheets

U.S. PATENT DOCUMENTS

| | | |
|---|---|---|
| 3,977,555 A | 8/1976 | Larson |
| 3,993,063 A | 11/1976 | Larrabee |
| 4,020,839 A | 5/1977 | Klapp |
| 4,051,852 A | 10/1977 | Villari |
| 4,109,670 A | 8/1978 | Slagel |
| 4,187,848 A | 2/1980 | Taylor |
| 4,210,173 A | 7/1980 | Choksi et al. |
| D257,286 S | 10/1980 | Folkman |
| 4,253,501 A | 3/1981 | Ogle |
| 4,296,786 A | 10/1981 | Brignola |
| 4,314,586 A | 2/1982 | Folkman |
| D267,199 S | 12/1982 | Koenig |
| D271,421 S | 11/1983 | Fetterman |
| 4,434,823 A | 3/1984 | Hudspith |
| 4,475,915 A | 10/1984 | Sloane |
| 4,493,348 A | 1/1985 | Lemmons |
| D280,018 S | 8/1985 | Scott |
| 4,532,969 A | 8/1985 | Kwaan |
| 4,564,054 A | 1/1986 | Gustavsson |
| 4,576,211 A | 3/1986 | Valentini et al. |
| 4,588,396 A | 5/1986 | Stroebel et al. |
| 4,588,403 A | 5/1986 | Weiss et al. |
| D284,603 S | 7/1986 | Loignon |
| 4,604,093 A | 8/1986 | Brown et al. |
| 4,607,671 A | 8/1986 | Aalto et al. |
| 4,614,437 A | 9/1986 | Buehler |
| 4,638,975 A | 1/1987 | Iuchi et al. |
| 4,639,019 A | 1/1987 | Mittleman |
| 4,667,927 A | 5/1987 | Oscarsson |
| 4,676,530 A | 6/1987 | Nordgren et al. |
| 4,697,622 A | 10/1987 | Swift et al. |
| 4,721,133 A | 1/1988 | Sundblom |
| 4,729,401 A | 3/1988 | Raines |
| 4,743,229 A | 5/1988 | Chu |
| 4,743,243 A | 5/1988 | Vaillancourt |
| 4,758,235 A | 7/1988 | Tu |
| 4,759,756 A | 7/1988 | Forman et al. |
| 4,778,447 A | 10/1988 | Velde et al. |
| 4,787,898 A | 11/1988 | Raines |
| 4,834,152 A | 5/1989 | Howson et al. |
| 4,865,592 A | 9/1989 | Rycroft |
| 4,909,290 A | 3/1990 | Coccia |
| 4,967,797 A | 11/1990 | Manska |
| D314,050 S | 1/1991 | Sone |
| 4,997,430 A | 3/1991 | Van der Heiden et al. |
| 5,035,686 A | 7/1991 | Crittenden et al. |
| 5,045,066 A | 9/1991 | Scheuble et al. |
| 5,049,129 A | 9/1991 | Zdeb et al. |
| 5,053,015 A | 10/1991 | Gross |
| 5,061,248 A | 10/1991 | Sacco |
| 5,088,996 A | 2/1992 | Kopfer et al. |
| 5,096,575 A | 3/1992 | Cosack |
| 5,104,387 A | 4/1992 | Pokorney et al. |
| 5,113,904 A | 5/1992 | Aslanian |
| 5,122,124 A | 6/1992 | Novacek et al. |
| 5,125,908 A | 6/1992 | Cohen |
| 5,171,230 A | 12/1992 | Eland et al. |
| 5,201,705 A | 4/1993 | Berglund et al. |
| 5,201,717 A * | 4/1993 | Wyatt et al. .................. 604/192 |
| 5,203,771 A | 4/1993 | Melker et al. |
| 5,203,775 A | 4/1993 | Frank et al. |
| 5,211,638 A | 5/1993 | Dudar et al. |
| 5,232,109 A | 8/1993 | Tirrell et al. |
| 5,247,972 A | 9/1993 | Tetreault |
| 5,269,768 A | 12/1993 | Cheung |
| 5,270,219 A | 12/1993 | DeCastro et al. |
| 5,279,576 A | 1/1994 | Loo et al. |
| 5,288,290 A | 2/1994 | Brody |
| 5,312,377 A | 5/1994 | Dalton |
| 5,328,474 A | 7/1994 | Raines |
| 5,334,163 A | 8/1994 | Sinnett |
| 5,342,346 A | 8/1994 | Honda et al. |
| 5,344,417 A | 9/1994 | Wadsworth, Jr. |
| 5,350,372 A | 9/1994 | Ikeda et al. |
| 5,364,387 A | 11/1994 | Sweeney |
| 5,374,264 A | 12/1994 | Wadsworth, Jr. |
| 5,385,547 A | 1/1995 | Wong et al. |
| 5,445,630 A | 8/1995 | Richmond |
| 5,464,123 A | 11/1995 | Scarrow |
| 5,466,219 A | 11/1995 | Lynn et al. |
| 5,466,220 A | 11/1995 | Brenneman |
| 5,478,337 A | 12/1995 | Okamoto et al. |
| 5,492,147 A | 2/1996 | Challender et al. |
| 5,505,714 A | 4/1996 | Dassa et al. |
| 5,509,433 A | 4/1996 | Paradis |
| 5,520,659 A | 5/1996 | Hedges |
| 5,526,853 A | 6/1996 | McPhee et al. |
| 5,531,695 A | 7/1996 | Swisher |
| 5,566,729 A | 10/1996 | Grabenkort et al. |
| 5,569,191 A | 10/1996 | Meyer |
| 5,573,281 A | 11/1996 | Keller |
| 5,578,015 A | 11/1996 | Robb |
| 5,583,052 A | 12/1996 | Portnoff et al. |
| 5,584,819 A | 12/1996 | Kopfer |
| 5,591,143 A | 1/1997 | Trombley, III et al. |
| 5,607,439 A | 3/1997 | Yoon |
| 5,611,576 A | 3/1997 | Guala |
| 5,616,203 A | 4/1997 | Stevens |
| 5,636,660 A | 6/1997 | Pfleiderer et al. |
| 5,641,010 A | 6/1997 | Maier |
| 5,647,845 A | 7/1997 | Haber et al. |
| 5,651,776 A | 7/1997 | Appling et al. |
| 5,653,686 A | 8/1997 | Coulter et al. |
| 5,674,195 A | 10/1997 | Truthan |
| 5,718,346 A | 2/1998 | Weiler |
| D393,722 S | 4/1998 | Fangrow, Jr. et al. |
| 5,738,144 A | 4/1998 | Rogers |
| 5,743,312 A | 4/1998 | Pfeifer et al. |
| 5,746,733 A | 5/1998 | Capaccio et al. |
| 5,755,696 A | 5/1998 | Caizza |
| 5,772,630 A | 6/1998 | Ljungquist |
| 5,772,652 A | 6/1998 | Zielinski |
| RE35,841 E | 7/1998 | Frank et al. |
| 5,820,621 A | 10/1998 | Yale et al. |
| 5,827,262 A | 10/1998 | Neftel et al. |
| 5,832,971 A | 11/1998 | Yale et al. |
| 5,833,213 A | 11/1998 | Ryan |
| 5,834,744 A | 11/1998 | Risman |
| 5,873,872 A | 2/1999 | Thibault et al. |
| 5,879,337 A | 3/1999 | Kuracina et al. |
| 5,879,345 A | 3/1999 | Aneas |
| 5,887,633 A | 3/1999 | Yale et al. |
| 5,893,397 A | 4/1999 | Peterson et al. |
| 5,919,182 A | 7/1999 | Avallone |
| 5,944,700 A | 8/1999 | Nguyen et al. |
| 5,971,965 A | 10/1999 | Mayer |
| 5,989,237 A | 11/1999 | Fowles et al. |
| 6,003,566 A | 12/1999 | Thibault et al. |
| 6,004,278 A | 12/1999 | Botich et al. |
| 6,063,068 A | 5/2000 | Fowles et al. |
| D427,308 S | 6/2000 | Zinger |
| 6,080,132 A | 6/2000 | Cole et al. |
| 6,090,093 A | 7/2000 | Thibault et al. |
| 6,099,511 A | 8/2000 | Devos et al. |
| 6,113,583 A | 9/2000 | Fowles et al. |
| 6,139,534 A | 10/2000 | Niedospial, Jr. et al. |
| 6,142,446 A | 11/2000 | Leinsing |
| 6,156,025 A | 12/2000 | Niedospial, Jr. et al. |
| 6,159,192 A | 12/2000 | Fowles et al. |
| 6,174,304 B1 | 1/2001 | Weston |
| 6,221,041 B1 | 4/2001 | Russo |
| 6,221,054 B1 | 4/2001 | Martin et al. |
| 6,238,372 B1 | 5/2001 | Zinger et al. |
| 6,245,044 B1 | 6/2001 | Daw et al. |
| D445,501 S | 7/2001 | Niedospial, Jr. |
| 6,280,430 B1 | 8/2001 | Neftel et al. |
| 6,343,629 B1 | 2/2002 | Wessman et al. |
| 6,348,044 B1 | 2/2002 | Coletti et al. |
| 6,358,236 B1 | 3/2002 | DeFoggi et al. |
| 6,379,340 B1 | 4/2002 | Zinger et al. |
| 6,408,897 B1 | 6/2002 | Laurent et al. |
| 6,409,708 B1 | 6/2002 | Wessman |
| 6,474,375 B2 | 11/2002 | Spero et al. |
| 6,478,788 B1 | 11/2002 | Aneas |
| D468,015 S | 12/2002 | Horppu |
| 6,503,240 B1 | 1/2003 | Niedospial, Jr. et al. |
| 6,503,244 B2 | 1/2003 | Hayman |

| | | |
|---|---|---|
| 6,524,278 B1 | 2/2003 | Campbell et al. |
| D472,316 S | 3/2003 | Douglas et al. |
| 6,530,903 B2 | 3/2003 | Wang et al. |
| D472,630 S | 4/2003 | Douglas et al. |
| 6,544,246 B1 | 4/2003 | Niedospial, Jr. |
| 6,551,299 B2 | 4/2003 | Miyoshi et al. |
| 6,558,365 B2 | 5/2003 | Zinger et al. |
| 6,581,593 B1 | 6/2003 | Rubin et al. |
| D483,487 S | 12/2003 | Harding et al. |
| D483,869 S | 12/2003 | Tran et al. |
| 6,656,433 B2 | 12/2003 | Sasso |
| 6,666,852 B2 | 12/2003 | Niedospial, Jr. |
| 6,681,810 B2 | 1/2004 | Weston |
| 6,681,946 B1 | 1/2004 | Jansen et al. |
| 6,699,229 B2 | 3/2004 | Zinger et al. |
| 6,715,520 B2 | 4/2004 | Andreasson et al. |
| 6,729,370 B2 | 5/2004 | Norton et al. |
| 6,736,798 B2 | 5/2004 | Ohkubo et al. |
| 6,745,998 B2 | 6/2004 | Doyle |
| 6,752,180 B2 | 6/2004 | Delay |
| D495,416 S | 8/2004 | Dimeo et al. |
| D496,457 S | 9/2004 | Prais et al. |
| 6,832,994 B2 | 12/2004 | Niedospial, Jr. et al. |
| 6,852,103 B2 | 2/2005 | Fowles et al. |
| 6,875,203 B1 | 4/2005 | Fowles et al. |
| 6,875,205 B2 | 4/2005 | Leinsing |
| 6,878,131 B2 | 4/2005 | Novacek et al. |
| 6,890,328 B2 | 5/2005 | Fowles et al. |
| 6,901,975 B2 | 6/2005 | Aramata et al. |
| 6,949,086 B2 | 9/2005 | Ferguson et al. |
| RE38,996 E | 2/2006 | Crawford et al. |
| 6,997,917 B2 | 2/2006 | Niedospial, Jr. et al. |
| 7,024,968 B2 | 4/2006 | Raudabough et al. |
| 7,074,216 B2 | 7/2006 | Fowles et al. |
| 7,083,600 B2 | 8/2006 | Meloul |
| 7,150,735 B2 | 12/2006 | Hickle |
| 7,192,423 B2 | 3/2007 | Wong |
| 7,294,122 B2 | 11/2007 | Kubo et al. |
| D561,348 S | 2/2008 | Zinger et al. |
| 7,326,194 B2 | 2/2008 | Zinger et al. |
| 7,350,764 B2 | 4/2008 | Raybuck |
| 7,354,422 B2 | 4/2008 | Riesenberger et al. |
| 7,354,427 B2 | 4/2008 | Fangrow |
| 7,425,209 B2 | 9/2008 | Fowles et al. |
| 7,435,246 B2 | 10/2008 | Zihlmann |
| 7,452,348 B2 | 11/2008 | Hasegawa |
| 7,470,265 B2 | 12/2008 | Brugger et al. |
| 7,488,297 B2 | 2/2009 | Flaherty |
| 7,491,197 B2 | 2/2009 | Jansen et al. |
| 7,523,967 B2 | 4/2009 | Steppe |
| D595,420 S | 6/2009 | Suzuki et al. |
| D595,421 S | 6/2009 | Suzuki et al. |
| 7,540,865 B2 | 6/2009 | Griffin et al. |
| D595,862 S | 7/2009 | Suzuki et al. |
| D595,863 S | 7/2009 | Suzuki et al. |
| 7,611,487 B2 | 11/2009 | Woehr et al. |
| 7,611,502 B2 | 11/2009 | Daly |
| 7,632,261 B2 | 12/2009 | Zinger et al. |
| 7,695,445 B2 | 4/2010 | Yuki |
| 7,722,090 B2 | 5/2010 | Burton et al. |
| D616,984 S | 6/2010 | Gilboa |
| 7,731,678 B2 | 6/2010 | Tennican et al. |
| 7,743,799 B2 | 6/2010 | Mosler et al. |
| 7,758,082 B2 | 7/2010 | Weigel et al. |
| 7,771,383 B2 | 8/2010 | Truitt et al. |
| 7,799,009 B2 | 9/2010 | Niedospial, Jr. et al. |
| 7,803,140 B2 | 9/2010 | Fangrow, Jr. |
| 7,879,018 B2 | 2/2011 | Zinger et al. |
| 2001/0029360 A1 | 10/2001 | Miyoshi et al. |
| 2001/0051793 A1 | 12/2001 | Weston |
| 2002/0017328 A1 | 2/2002 | Loo |
| 2002/0087118 A1 | 7/2002 | Reynolds et al. |
| 2002/0087141 A1 | 7/2002 | Zinger et al. |
| 2002/0087144 A1 | 7/2002 | Zinger et al. |
| 2002/0121496 A1 | 9/2002 | Thiebault et al. |
| 2002/0123736 A1 | 9/2002 | Fowles et al. |
| 2002/0127150 A1 | 9/2002 | Sasso |
| 2002/0173752 A1 | 11/2002 | Polzin |
| 2003/0036725 A1 | 2/2003 | Lavi et al. |
| 2003/0100866 A1 | 5/2003 | Reynolds |
| 2003/0120209 A1 | 6/2003 | Jensen et al. |
| 2003/0153895 A1 | 8/2003 | Leinsing |
| 2003/0195479 A1 | 10/2003 | Kuracina et al. |
| 2003/0199846 A1 | 10/2003 | Fowles et al. |
| 2003/0199847 A1 | 10/2003 | Akerlund et al. |
| 2004/0044327 A1 | 3/2004 | Hasegawa |
| 2004/0073189 A1 | 4/2004 | Wyatt et al. |
| 2004/0153047 A1 | 8/2004 | Blank et al. |
| 2004/0181192 A1 | 9/2004 | Cuppy |
| 2004/0217315 A1 | 11/2004 | Doyle |
| 2004/0236305 A1 | 11/2004 | Jansen et al. |
| 2005/0148994 A1 | 7/2005 | Leinsing |
| 2006/0030832 A1 | 2/2006 | Niedospial et al. |
| 2006/0079834 A1 | 4/2006 | Tennican et al. |
| 2006/0089603 A1 | 4/2006 | Truitt et al. |
| 2006/0135948 A1 | 6/2006 | Varma |
| 2006/0253084 A1 | 11/2006 | Nordgren |
| 2007/0060904 A1 | 3/2007 | Vedrine et al. |
| 2007/0083164 A1 | 4/2007 | Barrelle et al. |
| 2007/0088252 A1 | 4/2007 | Pestotnik et al. |
| 2007/0088293 A1 | 4/2007 | Fangrow |
| 2007/0088313 A1 | 4/2007 | Zinger et al. |
| 2007/0106244 A1 | 5/2007 | Mosler et al. |
| 2007/0156112 A1 | 7/2007 | Walsh |
| 2007/0167904 A1 | 7/2007 | Zinger et al. |
| 2007/0191760 A1 | 8/2007 | Iguchi et al. |
| 2007/0191764 A1 | 8/2007 | Zihlmann |
| 2007/0191767 A1 | 8/2007 | Hennessy et al. |
| 2007/0219483 A1 | 9/2007 | Kitani et al. |
| 2007/0255202 A1 | 11/2007 | Kitani et al. |
| 2007/0265574 A1 | 11/2007 | Tennican et al. |
| 2007/0265581 A1 | 11/2007 | Funamura et al. |
| 2007/0270778 A9 | 11/2007 | Zinger et al. |
| 2007/0287953 A1 | 12/2007 | Ziv et al. |
| 2008/0009789 A1 | 1/2008 | Zinger et al. |
| 2008/0172024 A1 | 7/2008 | Yow |
| 2008/0249479 A1 | 10/2008 | Zinger et al. |
| 2009/0012492 A1 | 1/2009 | Zihlmann |
| 2009/0054834 A1 | 2/2009 | Zinger et al. |
| 2009/0082750 A1 | 3/2009 | Denenburg et al. |
| 2009/0177177 A1 | 7/2009 | Zinger et al. |
| 2009/0187140 A1 | 7/2009 | Racz |
| 2009/0299325 A1 | 12/2009 | Vedrine et al. |
| 2010/0010443 A1 | 1/2010 | Morgan et al. |
| 2010/0030181 A1 | 2/2010 | Helle et al. |
| 2010/0076397 A1 | 3/2010 | Reed et al. |
| 2010/0087786 A1 | 4/2010 | Zinger et al. |
| 2010/0228220 A1 | 9/2010 | Zinger et al. |
| 2010/0312220 A1 | 12/2010 | Kalitzki |

FOREIGN PATENT DOCUMENTS

| | | |
|---|---|---|
| DE | 4122476 A1 | 1/1993 |
| DE | 19504413 A1 | 8/1996 |
| DE | 202004012714 U1 | 11/2004 |
| EP | 0192661 A1 | 9/1986 |
| EP | 0195018 A1 | 9/1986 |
| EP | 0258913 A2 | 3/1988 |
| EP | 0416454 A2 | 3/1991 |
| EP | 0 521 460 A1 | 1/1993 |
| EP | 0637443 A1 | 2/1995 |
| EP | 0 518 397 B1 | 2/1996 |
| EP | 0806597 A1 | 11/1997 |
| EP | 0814866 A1 | 1/1998 |
| EP | 0898951 A2 | 3/1999 |
| EP | 1008337 A1 | 6/2000 |
| EP | 1029526 A1 | 8/2000 |
| EP | 1051988 A2 | 11/2000 |
| EP | 1329210 A1 | 7/2003 |
| EP | 1454609 A1 | 9/2004 |
| EP | 1454650 A1 | 9/2004 |
| EP | 1498097 A2 | 1/2005 |
| EP | 1872824 A1 | 1/2008 |
| FR | 2029242 A5 | 10/1970 |
| FR | 2869795 A1 | 11/2005 |
| GB | 1444210 A | 7/1976 |
| JP | 4329954 A | 11/1992 |
| JP | 11503627 T | 3/1999 |
| WO | 9403373 A1 | 2/1994 |

| | | | |
|---|---|---|---|
| WO | 95/07066 A1 | 3/1995 |
| WO | 9600053 A1 | 1/1996 |
| WO | 96/29113 A1 | 9/1996 |
| WO | 9832411 A1 | 7/1998 |
| WO | 9837854 A1 | 9/1998 |
| WO | 0128490 A1 | 4/2001 |
| WO | 0130425 A1 | 5/2001 |
| WO | 0132524 A1 | 5/2001 |
| WO | 0160311 A1 | 8/2001 |
| WO | 0191693 A2 | 12/2001 |
| WO | 02/09797 A1 | 2/2002 |
| WO | 03/051423 A2 | 6/2003 |
| WO | 2004041148 A1 | 5/2004 |
| WO | 2005105014 A2 | 11/2005 |
| WO | 2007015233 A1 | 2/2007 |
| WO | 2007105221 A1 | 9/2007 |
| WO | 2009029010 A1 | 3/2009 |
| WO | 2009038860 A2 | 3/2009 |
| WO | 2009040804 A2 | 4/2009 |
| WO | 2009087572 A1 | 7/2009 |
| WO | 2009093249 A1 | 7/2009 |
| WO | 2009112489 A1 | 9/2009 |

OTHER PUBLICATIONS

The MixJect transfer system, as shown in the article, "Advanced Delivery Devices," Drug Delivery Technology Jul./Aug. 2007 vol. 7 No. 7 [on-line]. [Retrieved from Internet May 14, 2010.] URL: <http://www.drugdeiverytech-online.com/drugdelivery/200707/?pg=28pg28>. (3 pages).
Publication date of Israeli Patent Application 186290 [on-line]. ]Retrieved from Internet May 24, 2010]. URL:<http://www.ilpatsearch.justice.gov.il/UI/RequestsList.aspx>. (1 page).
Int'l Search Report issued Nov. 25, 2010 in Int'l Application No. PCT/IL2010/000530.
Office Action issued Feb. 7, 2011 in U.S. Appl. No. 12/783,194.
Office Action issued Dec. 20, 2010 in U.S. Appl. No. 12/063,176.
Office Action issued Dec. 13, 2010 in U.S. Appl. No. 12/293,122.
Office Action issued Dec. 23, 2010 in U.S. Appl. No. 29/334,696.
Grifols Vial Adapter Product Literature, 2 pages, Jan. 2002.
Novel Transfer, Mixing and Drug Delivery Systems, MOP Medimop Medical Projects Ltd. Catalog, 4 pages, Rev. 4, 2004.
Smart Site.RTM. Alaris Medical Systems Product Brochure, 4 pages, Issue 1, Oct. 1999.
Smart Site.RTM. Needle Systems, Alaris Medical Systems Webpage, 4 pages, Feb. 2006.
Photographs of Alaris Medical Systems SmartSite.RTM. device, 5 pages, 2002.
Non-Vented Vial Access Pin with ULTRASITE.RTM. Valve, B. Braun Medical, Inc. website and product description, 3 pages, Feb. 2006.
Office Action Issued Oct. 6, 2003 in U.S. Appl. No. 10/062,796.
Office Action Issued Feb. 22, 2005 in U.S. Appl. No. 10/062,796.
Office Action Issued Oct. 5, 2005 in U.S. Appl. No. 10/062,796.
Office Action Issued Feb. 20, 2009 in U.S. Appl. No. 11/694,297.
Int'l Search Report Issued Dec. 6, 2006 in Int'l Application No. PCT/IL2006/000912.
Int'l Preliminary Report on Patentability Issued Dec. 4, 2007 in Int'l Application No. PCT/IL2006/000912.
http://www.westpharma.com/eu/en/products/Pages/Mixject.aspx.
http://www.westpharma.com/eu/SiteCollectionDocuments/Recon/mixject%20product%20sheet.pfg: MIXJECT product information sheet pp. 1.
Int'l Search Report Issued Jul. 27, 2007 in Int'l Application No. PCT/IL2007/000343.
Int'l Preliminary Report on Patentability Issued Jun. 19, 2008 in Int'l Application No. PCT/IL2007/000343.
Int'l Search Report Issued Mar. 27, 2009 in Int'l Application No. PCT/US2008/070024.
Int'l Search Report Issued Oct. 17, 2005 in Int'l Application No. PCT/IL2005/000376.
Int'l Preliminary Report on Patentability Issued Jun. 19, 2006 in Int'l Application No. PCT/IL2005/000376.
Written Opinion of ISR Issued in Int'l Application No. PCT/IL2005/000376, Oct. 29, 2006.
Int'l Search Report Issued Aug. 25, 2008 in Int'l Application No. PCT/IL2008/000517.
Written Opinion of the ISR Issued in Int'l Application No. PCT/IL08/00517, Oct. 17, 2009.
Int'l Preliminary Report on Patenability Issued Oct. 20, 2009 in Int'l Application No. PCT/IL2008/000517.
Written Opinion of the Int'l Searching Authority Issued Oct. 27, 2008 in Int'l Application No. PCT/US2008/070024.
Int'l Search Report Issued Mar. 12, 2009 in Int'l Application No. PCT/IL2008/001278.
Office Action Issued in JP Application No. 2007-510229, Jan. 20, 2011.
Office Action Issued Apr. 20, 2010 in U.S. Appl. No. 11/997,569.
Int'l Search Report dated Nov. 20, 2006 in Int'l Application No. PCT/IL2006/000881.
Office Action Issued May 27, 2010 in U.S. Appl. No. 11/559,152.
Decision to Grant mailed Apr. 12, 2010 in EP Application No. 08738307.1.
Int'l Search Report issued Feb. 3, 2011 in Int'l Application No. PCT/IL2010/000777.
Int'l Search Report issued on Mar. 17, 2011 in Int'l Application No. PCT/IL2010/000854.
http://www.knovel.com/web/portal/browse/display?_EXT_KNOVEL_DISPLAY_bookid=1023&VerticalID=0 [retrieved on Feb. 9, 2011].
Int'l Search Report issued on Mar. 17, 2011 in Int'l Application No. PCT/IL2010/00915.
Office Action Issued May 12, 2011 in U.S. Appl. No. 12/063,176.

* cited by examiner

LIQUID DRUG MEDICAL DEVICE

CROSS-REFERENCE TO RELATED APPLICATIONS

This application is a Section 371 of International Application No. PCT/IL2005/00376, filed Apr. 6, 2005, which was published in the English language on Nov. 10, 2005, under International Publication No. WO 2005/105014 A2, which claims priority to U.S. Provisional Application Nos. 60/587,550, filed Jul. 14, 2004 and 60/589,568, filed Jul. 21, 2004, the disclosures of which are incorporated herein by reference in their entirety.

BACKGROUND OF THE INVENTION

The invention pertains to liquid drug medical devices, and needle shield removal devices.

Commonly owned PCT International Application No. PCT/US96/03732 published under PCT International Publication No. WO96/29113 illustrates and describes fluid control devices for administration of liquid drugs. The fluid control devices include inter alia fluid control devices now commercially available from Medimop Medical Projects Ltd, Ra'anana, Israel (www.medimop.com), under the registered trademark MIXJECT®. The MIXJECT® fluid control devices have a longitudinal axis, and include a base member with a syringe port for receiving a syringe, and a dispensing port in the form of a plastic cannula, a needle, and the like. The base member rotatably supports a flow control member with a manually rotatable vial adapter coupled thereto for rotating same between a first flow control position for connecting the syringe port with a vial received within the vial adapter, and a second flow control position for connecting the syringe port with the dispensing port (see WO96/29113's FIGS. 1-19). The vial adapter is preferably screw threadingly detachable from the base member at the second flow control position along a line of detachment transversely directed to the fluid control device's longitudinal axis (see WO96/29113's FIGS. 11-16).

Conventional needles have a female Luer connector for sealingly fitting on conventional syringes having a male Luer connector. Some syringes are made with a syringe tip having a distal end with a projecting lip to positively prevent a conventional needle being mounted thereon. However, such syringes are undesirably precluded from being used with other transfer devices having a female Luer connector, for example, vial adapters commercially available from Medimop Medical Projects Ltd, Ra'anana, Israel. Moreover, conventional needles are often supplied with needle shields for preventing needle sticks injuries. Needle shields are friction fitted on needles and are often difficult to remove in part due to their small dimensions which render them difficult to grasp. Exemplary needle shield removal devices are illustrated and described in inter alia EP 0 518 397 entitled "Device for the removal and replacement of a needle shield", WO 02/09797 entitled "Pen Needle and Safety Shield System", and WO2003/051423 entitled "Needle Closure System Removal Device".

BRIEF SUMMARY OF THE INVENTION

In accordance with a first aspect of the present invention, there is provided a liquid drug medical device for use with a source of physiological solution and a medicinal vessel for administration of a liquid drug, the device having a longitudinal axis and comprising:

(a) a body member having a first port for fluid connection with the source of physiological solution;
(b) a flow control member rotatably mounted in said body member about an axis of rotation co-directional with the longitudinal axis, and having a first major flow duct and a second major flow duct substantially parallel to and non-coaxial with said axis of rotation and respectively terminating at a second port, and a third port for administering the liquid drug; and
(c) a manually rotatable adapter having a fluid conduit member with a proximal end in flow communication with said second port and a distal end extending into the medicinal vessel on its attachment to said adapter, and coupled to said flow control member for rotating same between a first flow control position for connecting said first port with said second port, and a second flow control position for connecting said first port with said third port.

Liquid drug medical devices of the present invention preferably include an adapter detachable along a line of detachment co-directional with the drug medical device's longitudinal axis thereby affording a more ergonomic inline detachment than the hitherto aforementioned MIXJECT® fluid control devices with transversely directed lines of detachment. Such liquid drug medical devices with detachable adapters also lend themselves to more compact devices affording improved handling, and preferably include drug dispensers, for example, a built-in needle, an atomizer, and the like, in fluid connection with their third ports suitable for self-administration of a liquid drug. Different adapters can be designed suitable for use with different medicinal vessels including inter alia vials, ampoules, and the like.

In accordance with a second aspect of the present invention, there is provided a liquid drug medical device for use with a syringe having a syringe tip with a distal end having a projecting lip, and a medicinal vial with a rubber stopper, the device comprising an adapter for snap fitting onto the vial and including a hollow puncturing member for puncturing the rubber stopper on snap fitting said adapter on the vial, and an elastomer tubing in flow communication with said puncturing member and having a distal end capable of being sealingly stretched over the syringe's projecting lip for effecting fluid communication between the syringe and the medicinal vial. Thus, the liquid drug transfer device is adapted for convenient use with syringes prevented from having conventional needles with a female Luer connector slidingly mounted thereon.

In accordance with a third aspect of the present invention, there is provided a needle shield removal device for use with a liquid drug medical device with a needle protected by a needle shield, the needle including a hub with a flange rim, and a needle stick, the needle shield removal device comprising:

(a) a base member including at least two spaced apart support legs terminating at end faces; and
(b) a needle shield release member including a pair of oppositely directed finger supports, and at least two spaced apart clamping legs interposed between said at least two spaced apart support legs and terminating at needle shield grips for bearing against the needle's flange rim for slidingly removing the needle shield from the needle, said needle shield release member being slidingly displaceable along said base member from an initial outwardly biased position in which said needle shield grips are substantially flush with said end faces and a retracted position in which said needle shield grips are inwardly disposed relative to said end faces, the needle shield removal device being slidingly mounted on the liquid drug medical device for enveloping the needle shield therewithin whereupon the needle shield release member is positively urged to said retracted position for entraining the needle shield therewith thereby safely exposing the needle stick.

BRIEF DESCRIPTION OF THE SEVERAL VIEWS OF THE DRAWINGS

In order to understand the invention and to see how it can be carried out in practice, preferred embodiments will now be described, by way of non-limiting examples only, with reference to the accompanying drawings in which similar parts are likewise numbered, and in which.

In the drawings.

DETAILED DESCRIPTION OF THE INVENTION

Figure 1:
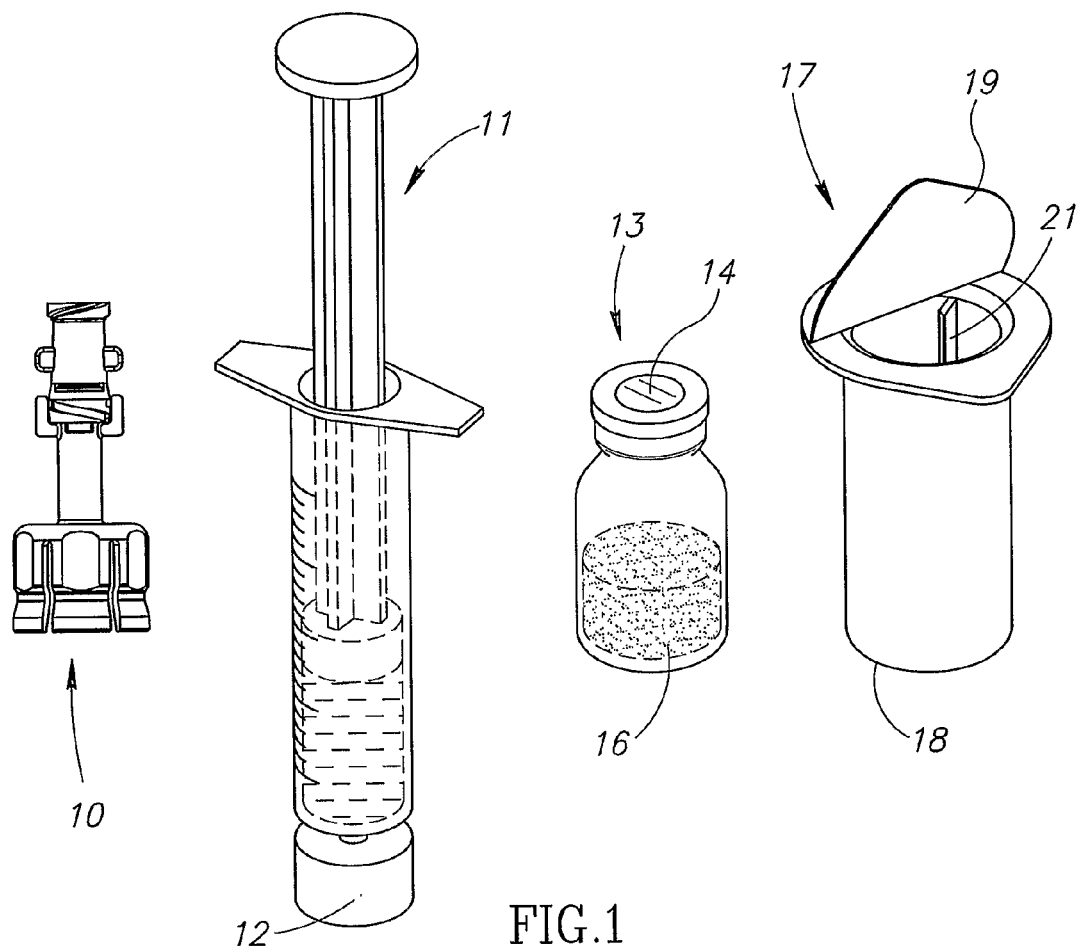
FIG. 1 is a pictorial view of a liquid drug medical device in accordance with the first aspect of the present invention, a pre-filled syringe, a vial containing a drug concentrate, and an empty packaging previously housing the liquid drug medical device.
Figure 2:
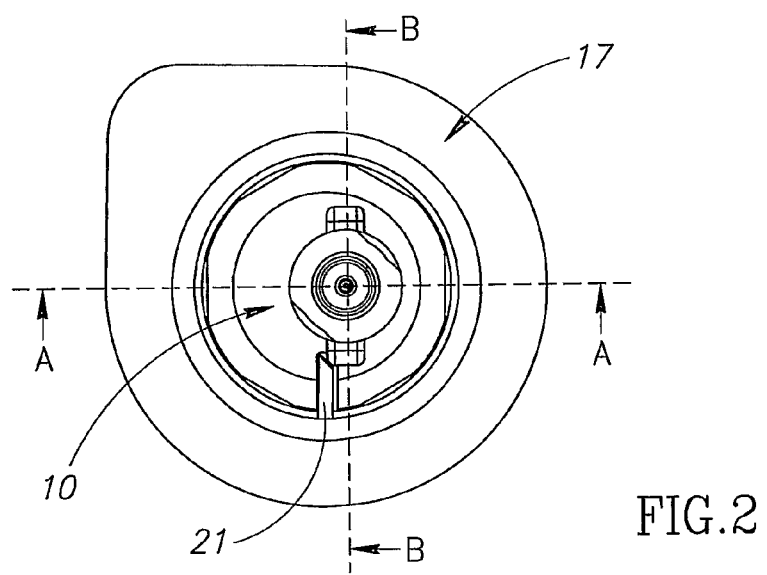
FIG. 2 is a top view of FIG. 1's packaging opened but prior to removal of the liquid drug medical device.

FIG. 1 shows a liquid drug medical device 10 for use with a typically pre-filled syringe 11 having a clockwise threaded male Luer lock connector 12, and a vial 13 having a rubber stopper 14 and containing a dry powder drug concentrate 16 but could equally contain a liquid drug concentrate. The liquid drug medical device 10 is designed to reconstitute the drug concentrate in the vial 13 for aspiration into the syringe 11 ready for typically self-administration. The liquid drug medical device 10 is typically packaged in a sealed sterile non-pyrogenic packaging 17 including a transparent plastic casing 18 with a peel off cover 19 shown partially removed for enabling removal of the liquid drug medical device 10. The casing 18 has a longitudinally directed stopper 21 for stopping rotation of the liquid drug medical device 10 at a set-up position pursuant to screwing the syringe 11 onto the liquid drug medical device 10 (see FIG. 2).

Figure 3:
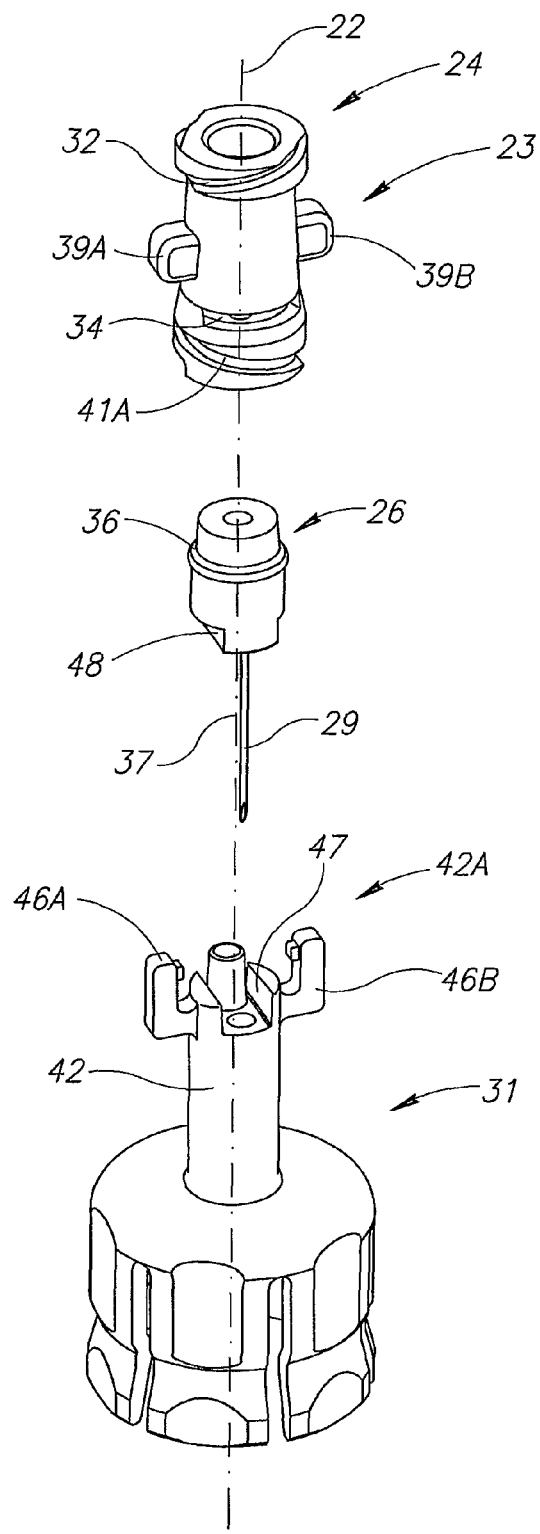
FIG. 3 is an exploded view of the liquid drug medical device of FIG. 1 having a built-in needle for administering a liquid drug to a subject.
Figure 4A:
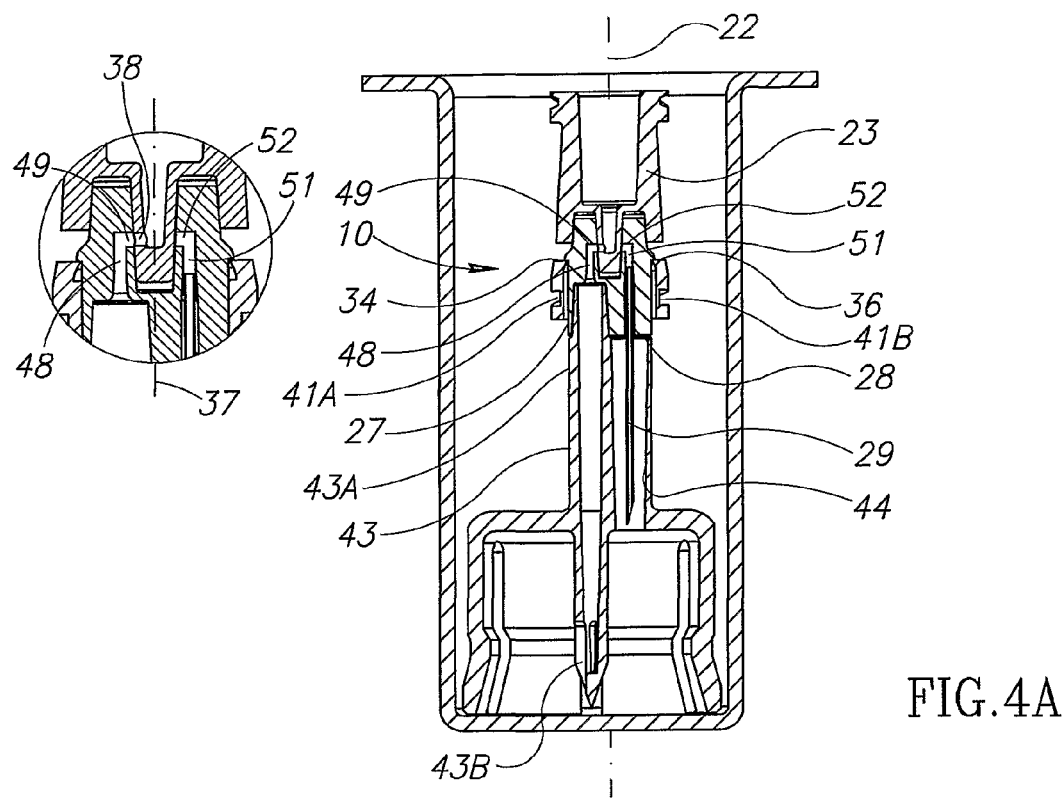
FIGS. 4A and 4B are cross sections respectively along lines A-A and B-B in FIG. 2 of FIG. 1's liquid drug medical device in its set-up position.
Figure 4B:
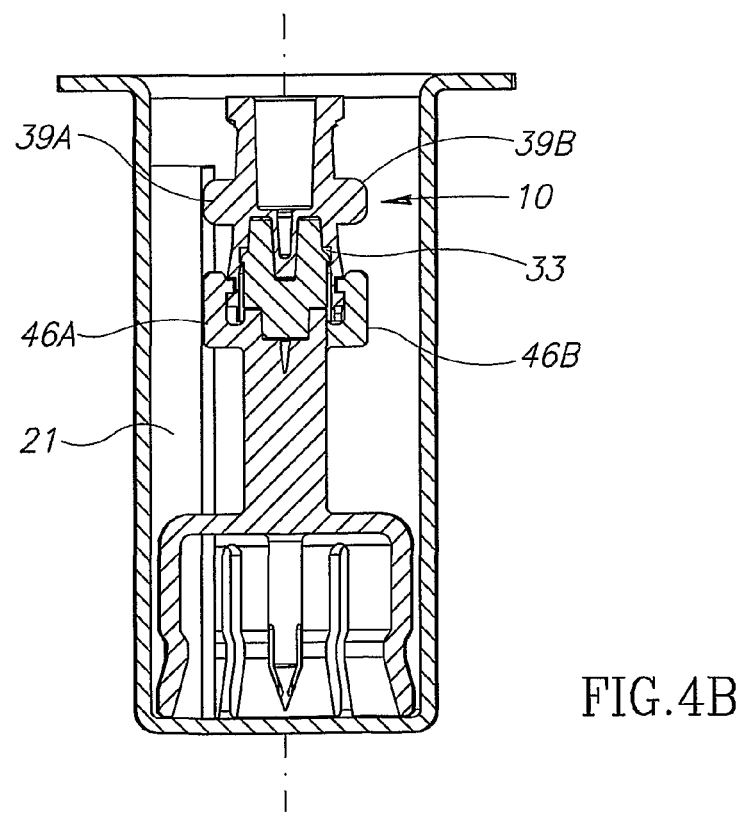

FIGS. 3 and 4 show that the liquid drug medical device 10 has a longitudinal axis 22, and includes a base member 23 having a first port 24, a flow control member 26 having a second port 27 and a third port 28 provided with a needle stick 29, and a vial adapter 31 (constituting an adapter) removably attachable to the base member 23. The first port 24 has a clockwise threaded female Luer connector 32 for screw threadingly receiving the syringe's clockwise threaded male Luer connector 12 in a clockwise direction. The base member 23 has a chamber 33 with an annular recess 34 for snap fit receiving an annular flange 36 formed on the flow control member 26 whereby the flow control member 26 is rotatably supported in the chamber 33 about an axis of rotation 37 co-axial with the longitudinal axis 22. The first port 24 is in fluid communication with the chamber 33 via a radially directed bore 38 perpendicular to the axis of rotation 37. The base member 23 has a pair of laterally protruding members 39A and 39B at its proximal end for stopping against the stopper 21, and a pair of half turn screw threads 41A and 41B for enabling screw thread engagement of the vial adapter 31 thereonto.

Figure 5A:
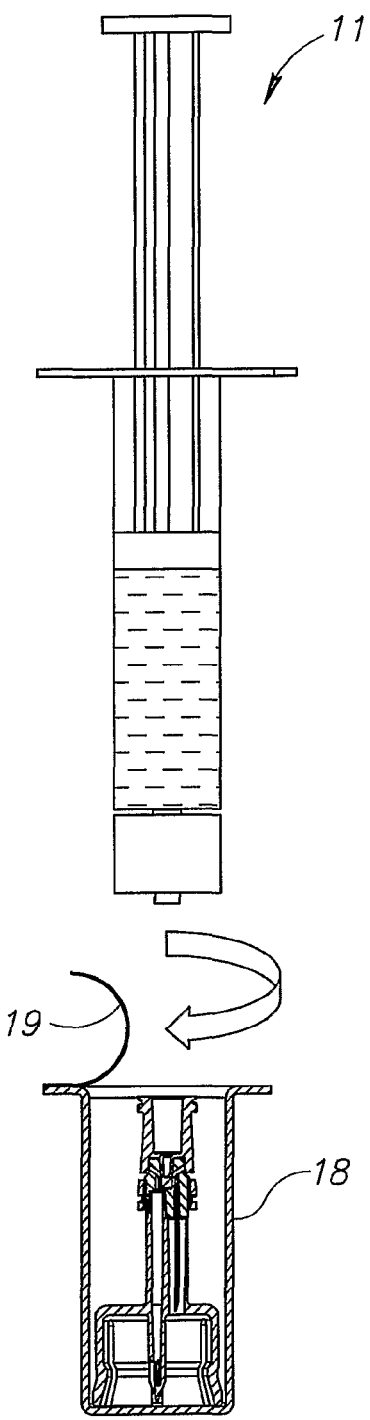
FIGS. 5A-5F show the use of FIG. 1's liquid drug medical device for preparing a liquid drug ready for administration to a subject.
Figure 5B:
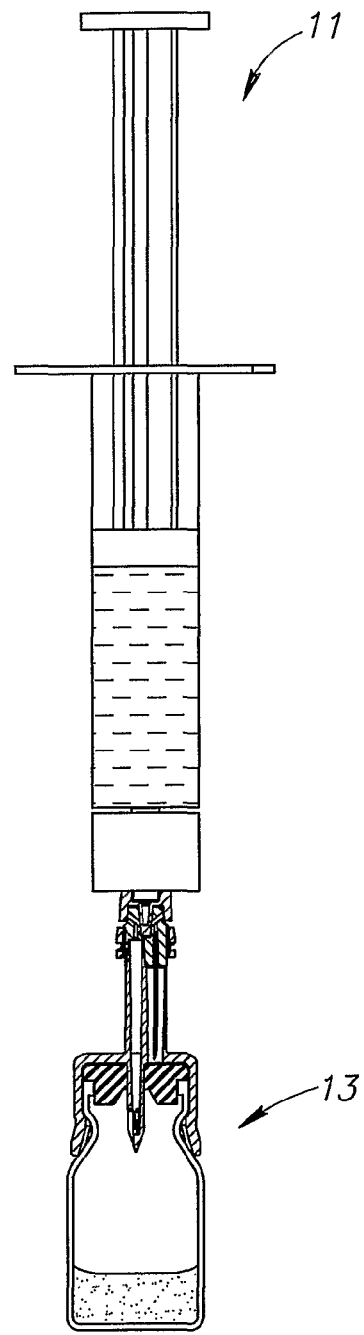
Figure 5C:
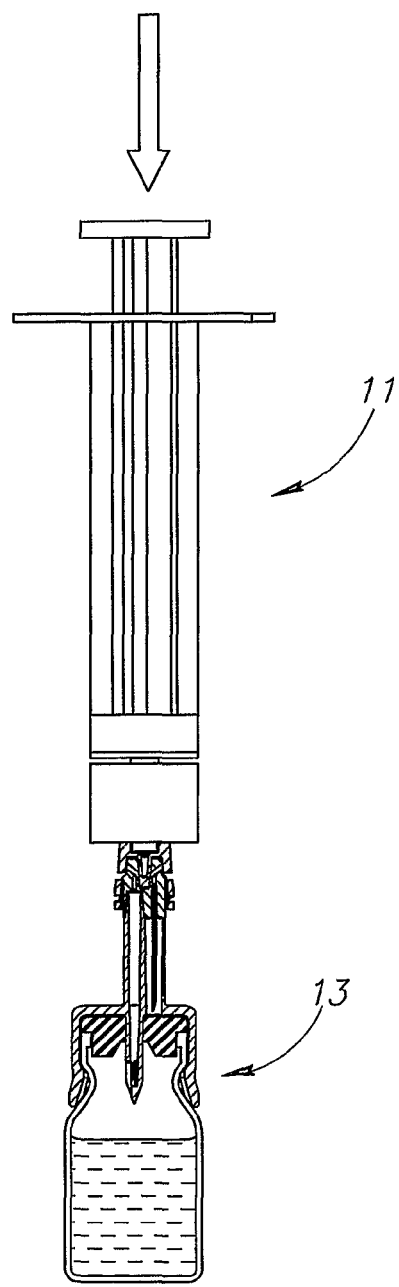
Figure 5D:
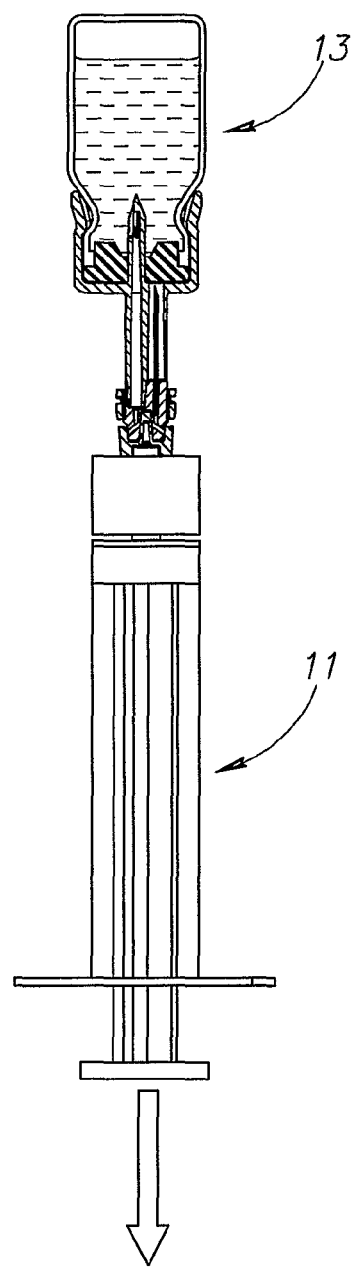
Figures 5E, 5F:
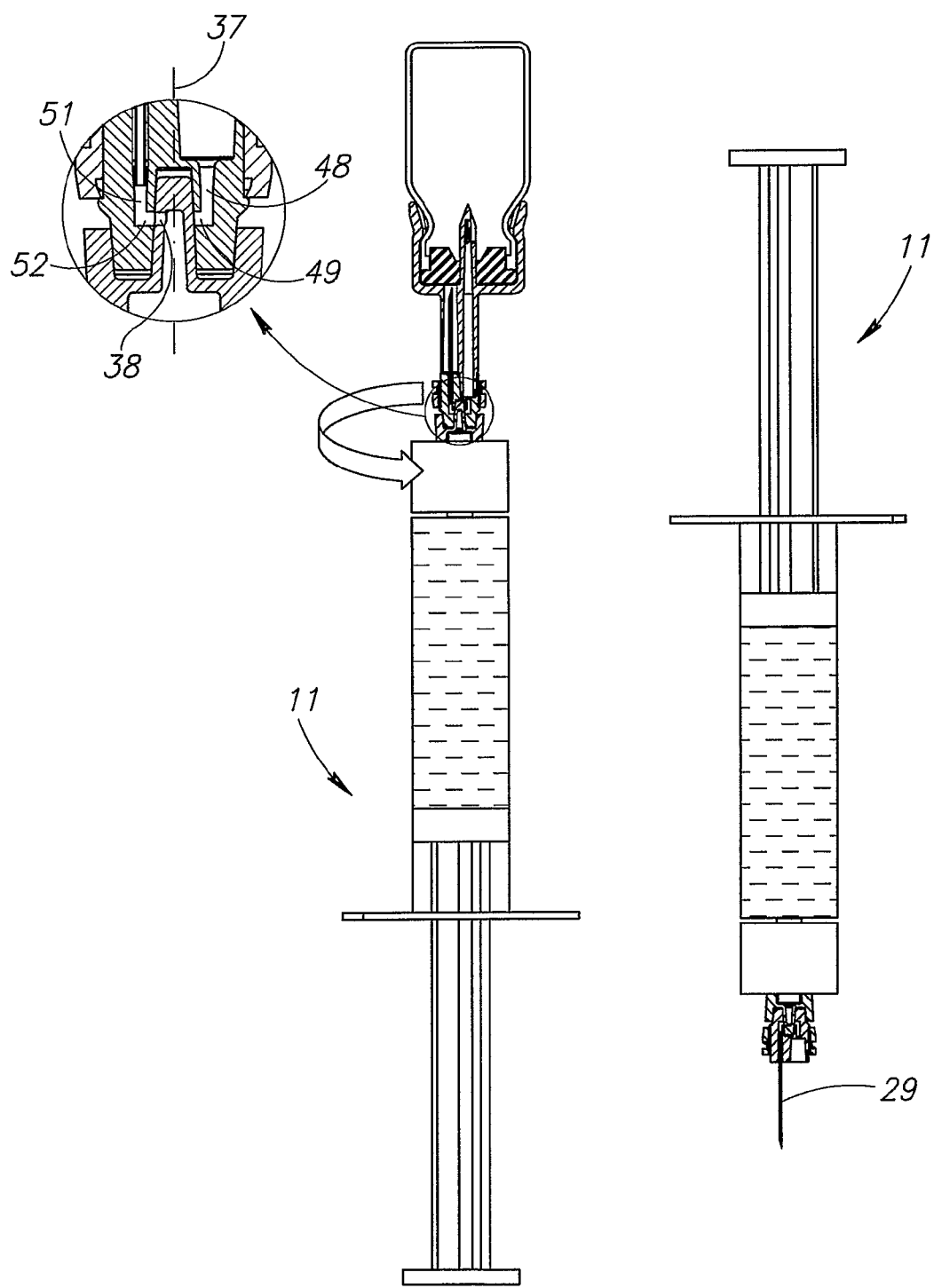

The vial adapter 31 has an elongated stem 42 including a fluid conduit member 43 with a proximal end 43A in fluid communication with the second port 27 on attachment of the vial adapter 31 on the base member 23, and a pointed distal end 43B for puncturing the vial's rubber stopper 14 on its positive insertion into the vial adapter 31 and extending slightly therebeyond so that on inverting the vial its nearly entire contents can be aspirated thereinto (see FIG. 5E). The stem 42 includes a bore 44 parallel to the fluid conduit member 43 and largely co-extensive therewith for accommodating the needle stick 29 therein on attachment on the vial adapter 31 on the body member 23. The stem 42 has a proximal end 42A with a pair of laterally protruding arms 46A and 46B for screw threading onto the pair of half turn screw threads 41A and 41B, and for stopping against the stopper 21. The screw threads 41A and 41B are screw threaded in a counter direction to the male and female threaded Luer connectors 12 and 32 such that screwing the syringe 11 onto the base member 23 causes the vial adapter 31 to be fully threaded onto the base member 23, and rotation of the liquid drug medical device 10 in the casing 18 such until both the base member's member 39A and the vial adapter's arm 46A abut against the stopper 21 thereby priming the liquid drug medical device 10 into its set-up position. The proximal end 42A is formed with a slot

47 for receiving a downward depending key 48 formed on the underside of the flow control member 26 thereby coupling the vial adapter 31 to the flow control member 26 such that manual rotation of the vial adapter 31 correspondingly rotates the flow control member 26.

The second port 27 is in flow communication with the first port 24 via a first major flow duct 48 parallel to and non-coaxial with the axis of rotation 37 and a first minor flow duct 49 in registration with the bore 38 in a first flow control position of the flow control member 26 in the set-up position of the liquid drug medical device 10 (see FIG. 4A). The third port 28 is in flow communication with the first port 24 via a second major flow duct 51 parallel to and non-coaxial with the axis of rotation 37 and a second minor flow duct 52 in registration with the bore 38 in a second flow control position of the flow control member 26 when the vial adapter 31 is rotated through a half turn ready for axial detachment from the base member 23 along a line of detachment co-directional with the longitudinal axis 22 (see FIG. 5E).

The use of the liquid drug medical device 10 is now described with reference to FIGS. 5A-5F:

The peel off cover 19 is removed from the casing 18 and a pre-filled syringe 11 is screw threaded clockwise onto the female Luer connector 32 (see FIG. 5A). The liquid drug medical device 10 may initially rotate within the casing 18 depending on its initial placement therein but stops rotating when primed into its set-up position. The liquid drug medical device 10 is withdrawn from the casing 18 and the vial 13 is positively inserted into the vial adapter 31 such that the fluid conduit member 43 punctures its rubber stopper 14 (see FIG. 5B). The syringe's contents are injected into the vial 13 (see FIG. 5C), and the entire assembly including the liquid drug medical device 10, the now empty syringe 11, and the vial 13 is shaken to reconstitute the vial's dry powder drug concentrate. The entire assembly is inverted and the syringe 11 is aspirated to draw the reconstituted liquid drug thereinto (see FIG. 5D). The vial adapter 31 is rotated through a half turn counterclockwise to rotate the flow control member 26 into its second flow control position for connecting the syringe 11 with the needle stick 29, and simultaneously enabling axial detachment of the vial adapter 31 with the spent vial 13 from the base member 23 (see FIG. 5E). The liquid drug medical device 10 is now ready for administering the reconstituted liquid drug via the still dry needle stick 29 to a subject (see FIG. 5F).

Figures 6, 7:
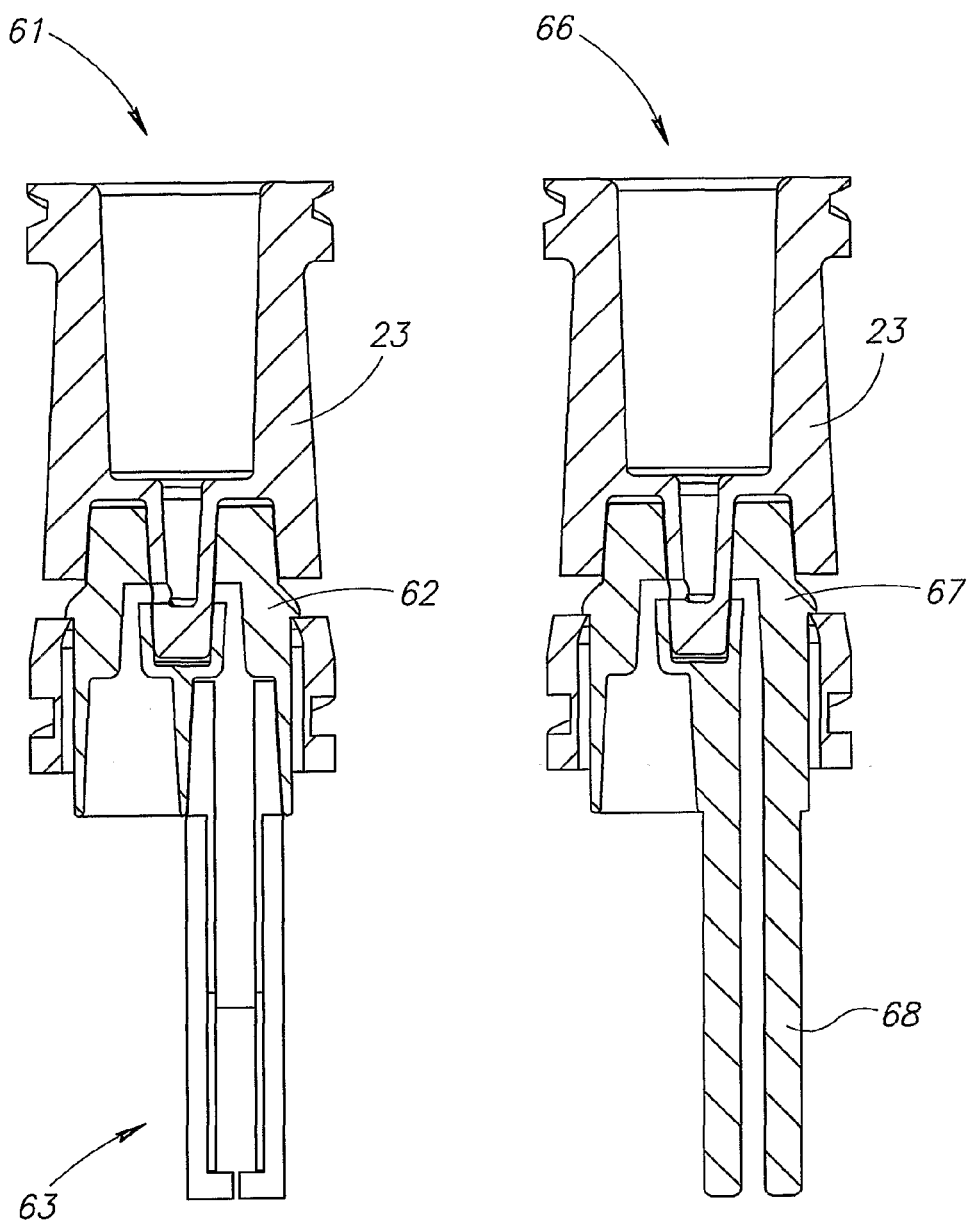
FIG. 6 is a cross section of a second preferred embodiment of a liquid drug medical device of the present invention including an atomizer.
FIG. 7 is a cross section of a third preferred embodiment of a liquid drug medical device of the present invention including a drug dispenser port.

FIG. 6 shows a liquid drug medical device 61 having a flow control member 62 provided with an atomizer 63.

FIG. 7 shows a liquid drug medical device 66 having a flow control member 67 provided with a drug dispenser port 68.

Figure 8:
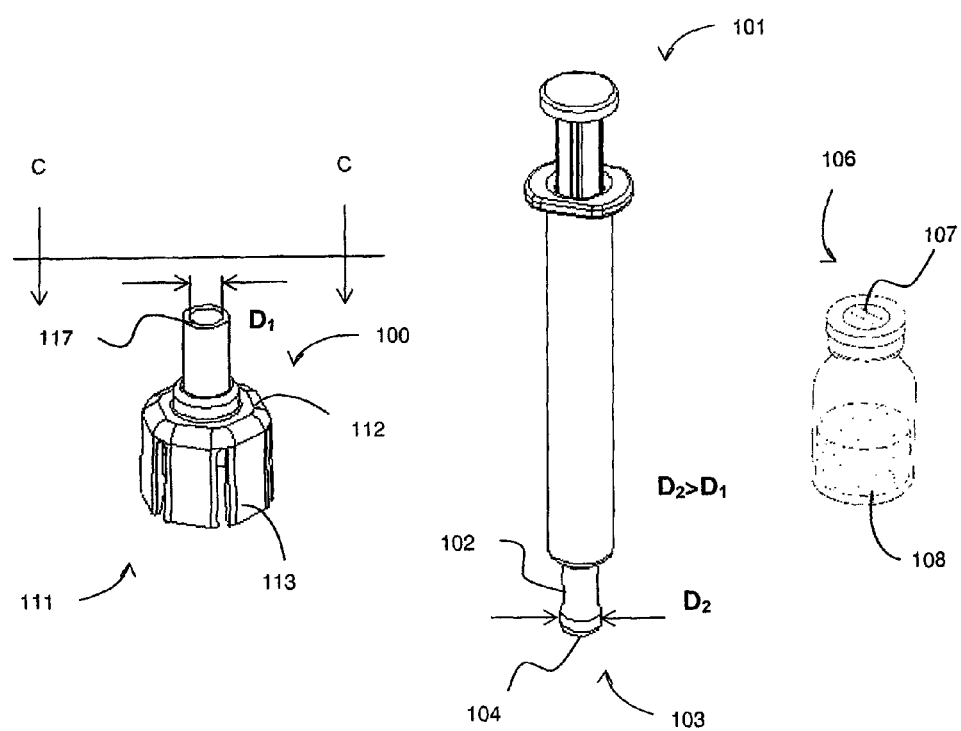
FIG. 8 is a perspective view of a liquid drug medical device in accordance with the second aspect of the present invention, a syringe with a syringe tip with a protruding lip, and a vial containing a drug concentrate.

FIG. 8 shows a liquid drug transfer device 100 for use with a syringe 101 having a syringe tip 102 with a distal tip 103 having a projecting lip 104 for blocking the sliding mounting of a conventional needle with a female Luer connector thereon, and a vial 106 having a rubber stopper 107 and containing a dry powder drug concentrate 108 but could equally contain a liquid drug concentrate. The liquid drug transfer device 100 includes a vial adapter 111 with a top wall 112, a resiliently deformable slitted skirt 113 for snap fitting onto the vial 106, and a hollow puncturing member 114 (see FIGS. 9-11) for puncturing the vial's rubber stopper 107, and an elastomer tubing 116 in flow communication with the puncturing member 114 and having a distal end 117 for sealingly fitting over the syringe's projecting lip 104 for enabling flow communication between the syringe 101 and the vial 106. The tubing 116 typically has a length L=10-20 mm and a nominal internal diameter D1=3-4 mm which can be readily stretched to at least 6 mm to sealingly fit over the projecting lip's diameter D2>D1 without tearing, ripping, and the like. The tubing 116 is preferably formed from one of the following substances: PVC, silicone, rubber, and the like.

Figure 9:
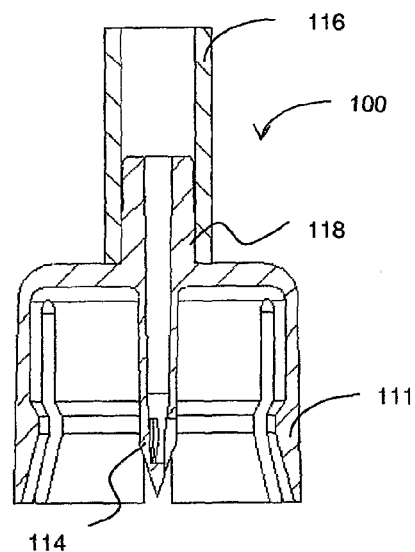
FIG. 9 is a longitudinal cross section of a first embodiment of FIG. 8's liquid drug medical device along line C-C in FIG. 8.
Figure 10:
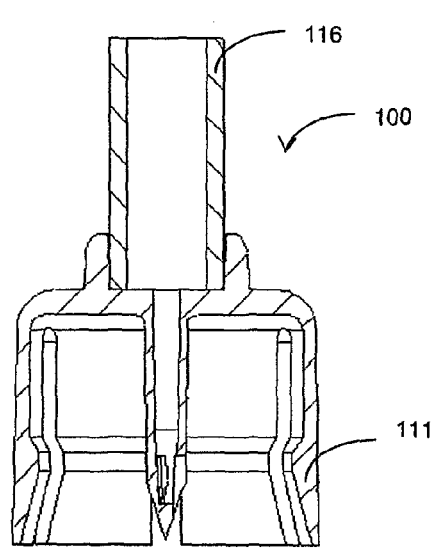
FIG. 10 is a longitudinal cross section of a second embodiment of FIG. 8's liquid drug medical device along line C-C in FIG. 8.
Figure 11:
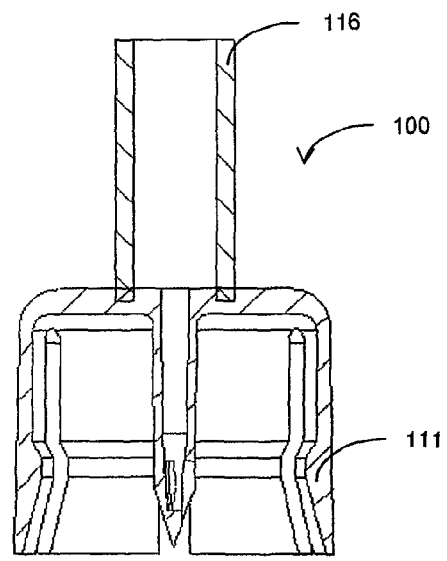
FIG. 11 is a longitudinal cross section of a third embodiment of FIG. 8's liquid drug medical device along line C-C in FIG. 8.
Figure 12:
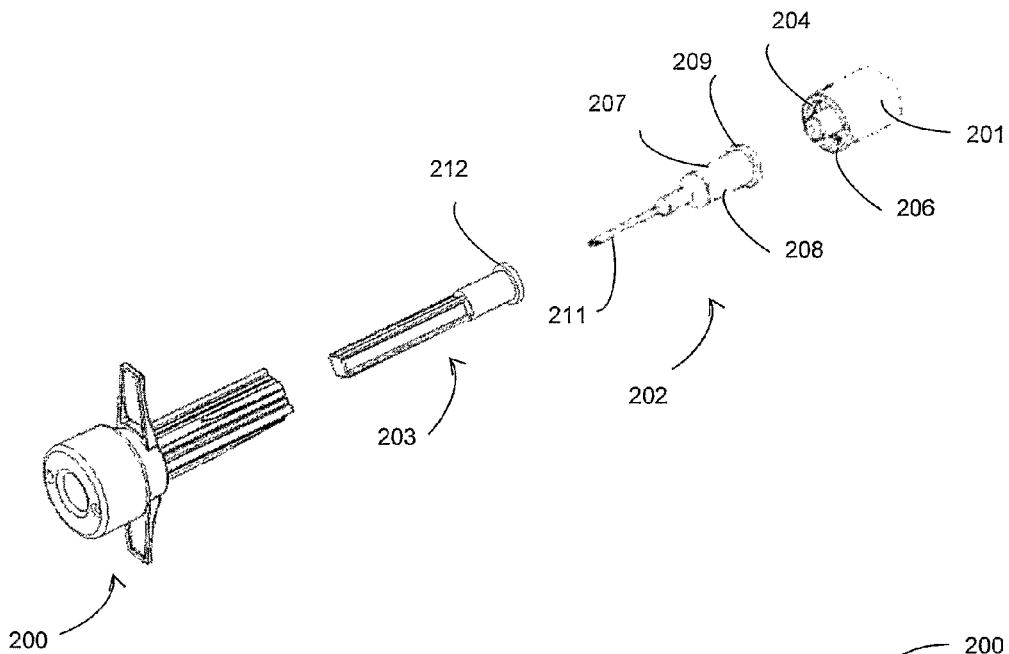
FIG. 12 is a perspective view of a syringe with a protected needle and a needle shield removal device in accordance with the third aspect of the present invention.

FIG. 9 shows a liquid drug transfer device 100 including a vial adapter 111 with an upright nipple 118 having tubing 116 press fitted or bonded thereon. FIG. 10 shows a liquid drug transfer device 100 having a vial adapter 111 over molded (or otherwise known as insert molded) around the tubing 116. FIG. 11 shows a liquid drug transfer device 100 manufactured using two material injection molding, namely, the vial adapter 111 and the tubing 116 are made in one and the same mold.

Figure 13:
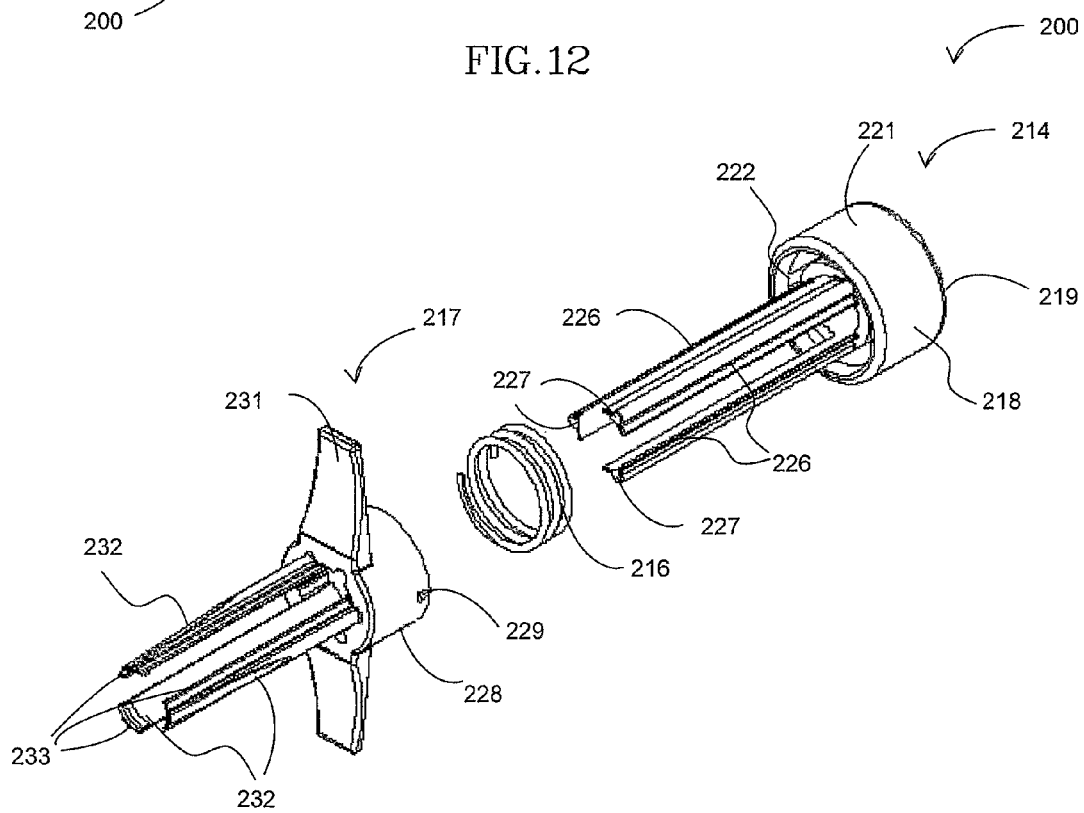
FIG. 13 is an exploded view of the needle shield removal device of FIG. 12.

FIG. 13 shows a needle shield removal device 200 for use with a liquid drug medical device 201 fitted with a needle 202 protected by a needle shield 203. The liquid drug medical device 201 can be in the form of a syringe, a MIXJECT® fluid control device commercially available from Medimop Medical Projects Ltd, Ra'anana, Israel, and the like. The liquid drug medical device 201 includes a male Luer lock connector 204 with a distal annular end face 206. The needle 202 includes a hub 207 with a ribbed surface 208 and a flange rim 209 for screw insertion into the male Luer lock connector 204, and a needle stick 211. The needle shield 203 includes a flanged rim 212 and is designed to snap fit onto the ribbed surface 208 to shield the needle stick 211 whereupon the flanged rim 212 is separated from the end face 206 by an about 1-2 mm gap. The needle shield removal device 200 is designed to positively slide the needle shield 203 by an about 1 mm-2 mm stroke sufficient to release the needle shield 203 from the liquid drug medical device 201, thereby safely and conveniently exposing the needle stick 211.

Figure 14:
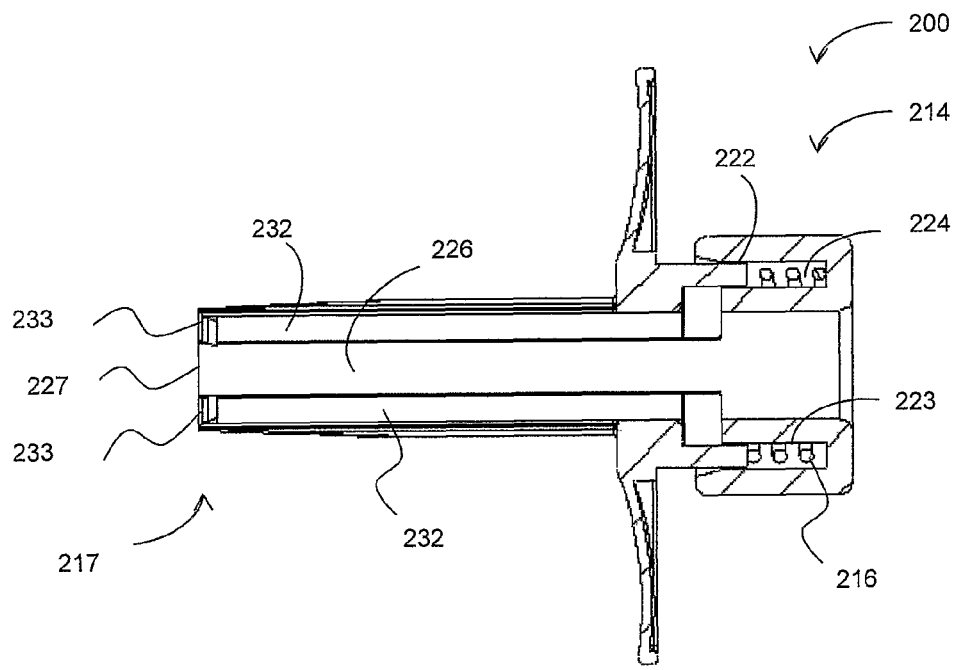
FIG. 14 is a longitudinal cross section of the needle shield removal device of FIG. 12 in its first operative state.

FIG. 14 shows the needle shield removal device 200 includes a triple-legged base member 214, a compression spring 216, and a triple legged needle shield release member 217. The base member 214 has a cap 218 with a top wall 219, an outer wall 221 with an undercut 222, and an inner wall 223 defining a tubular cavity 224 with the outer wall 221 for receiving the compression spring 216. The inner wall 223 is formed with three support legs 226 equidistanced therearound, and each occupying an arc angle of about 60°. The support legs 226 terminate in flat end faces 227 for abutment against the end face 206 on slidingly mounting the needle shield removal device 200 onto the liquid drug medical device 201 with the protected needle 202.

Figure 15:
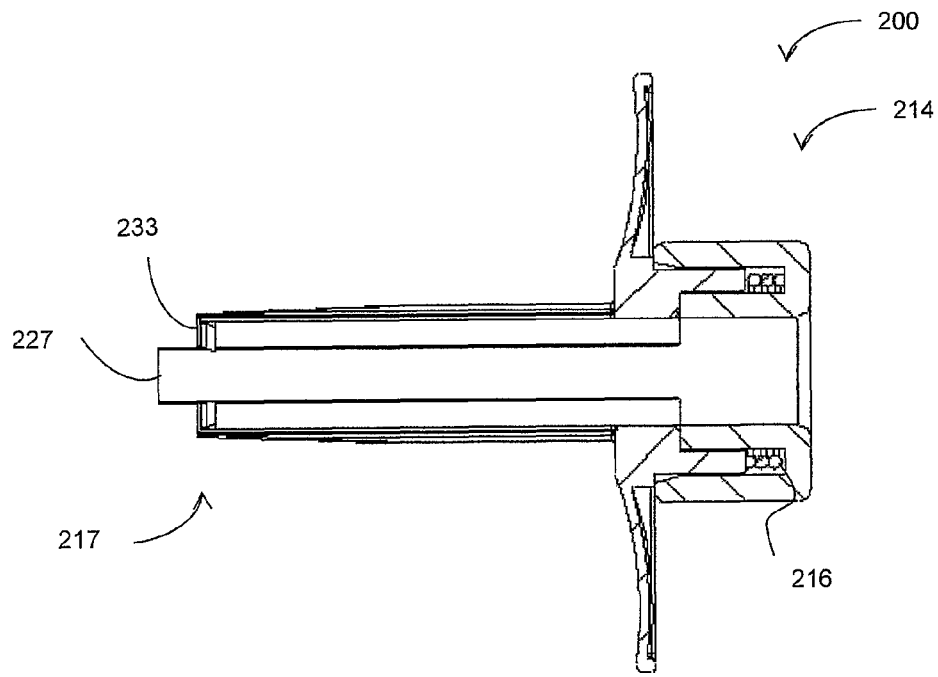
FIG. 15 is a longitudinal cross section of the needle shield removal device of FIG. 12 in its second operative state.
Figure 16:
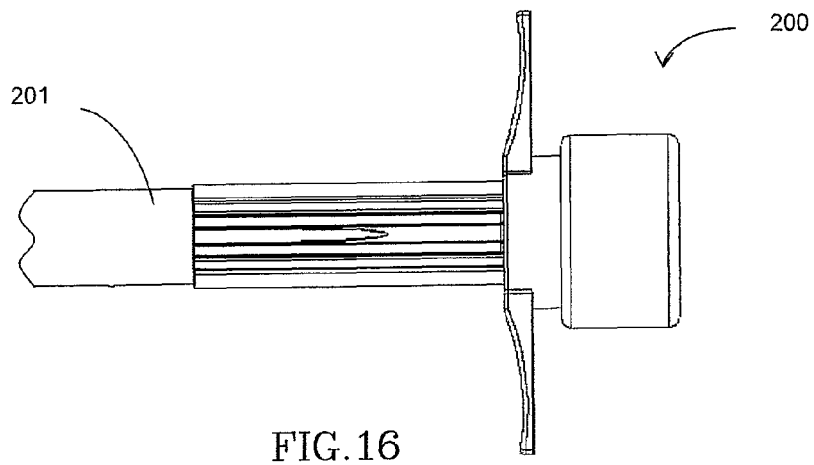
FIG. 16 is a longitudinal cross section showing placement of the needle shield removal device on a syringe with a protected needle.
Figure 17:
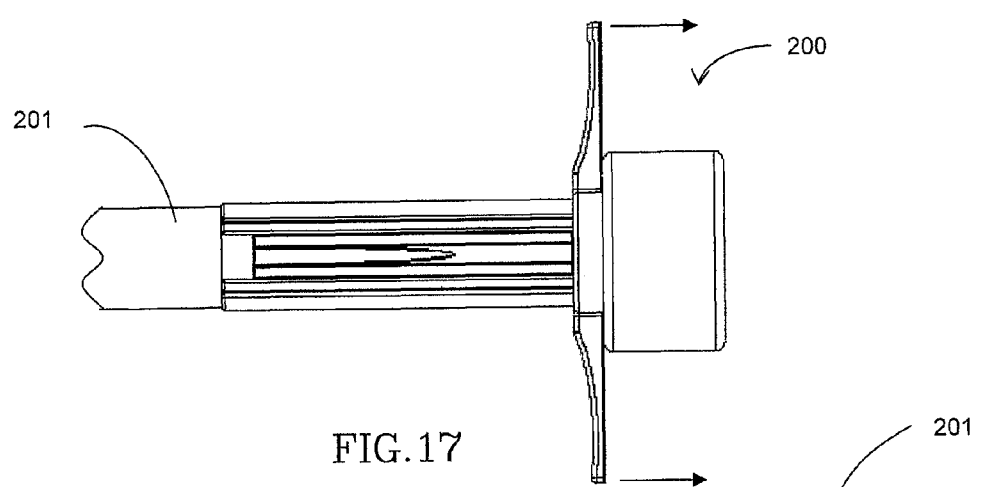
FIG. 17 is a longitudinal cross section showing detachment of the needle shield from the syringe to expose its needle.
Figure 18:
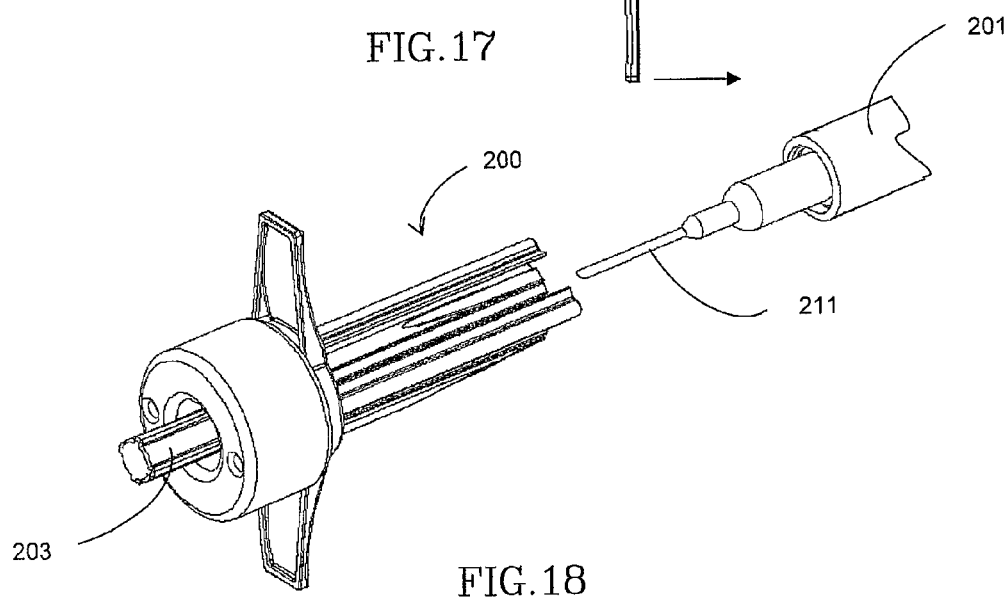
FIG. 18 is a longitudinal cross section showing removal of the needle shield removal device together with the needle from the syringe.

The needle shield release member 217 has an annular head 228 formed with a retaining tab 229 for stopping against the undercut 222 for retaining the needle shield release member 217 in the base member 214 on snap fit insertion of the head 228 into the tubular cavity 226. The head 228 has a pair of oppositely directed laterally extending finger supports 231 for enabling a compression force to be applied to the compression spring 16 for enabling the needle shield release member 217 to be positively urged into the base member 214 from an outward spring biased position (see FIG. 15) to an inward hand compressed position (see FIG. 16). The head 228 is formed with three needle shield clamping legs 232 equidistanced therearound and intended to be interposed between adjacent support legs 226 on assembly of the needle shield removal device 213. The needle shield release legs 232 also each occupy an arc angle of about 60° similar to the support legs 226 such that the needle shield removal device 213 circumscribes a needle shield 203 on its sliding mounting the liquid drug medical device 201 with the protected needle 202. The needle shield clamping legs 232 terminate in inwardly directed needle shield grips 233 flush with the end faces 227 in the outward spring biased position (see FIG. 14) and are intended for bearing against the needle shield's flange rim 212 facing the end face 206 on application of the compression force to positively draw the needle shield release member 217 into the base member 213.

The use of the needle shield removal device 200 is as follows:

The user holds the liquid drug medical device 201 with the protected needle 202 in one hand and the needle shield removal device 200 in his other hand. The user slidingly mounts the needle shield removal device 200 onto the liquid drug medical device 201 until the needle shield grips 233 snap fit over the flange rim 212 and the end faces 227 abut against the end face 206 (see FIG. 16). The user places his thumb on the top wall 219 and his digit finger and middle finger against the undersides of the finger supports 231 so that he can apply a compressive force to urge the needle shield release member 217 into the base member 214. The needle shield release member 217 by virtue of its needle shield grips 233 bearing against the needle shield's flange rim 212 entrains the needle shield 203 therewith, thereby safely and conveniently exposing the needle stick 211 for injection purposes. The user disposes of the spent liquid drug medical device 200 with its exposed needle stick 211 in a sharps container.

While the invention has been described with respect to a limited number of embodiments, it will be appreciated that many variations, modifications, and other applications of the invention can be made within the scope of the appended claims.

The invention claimed is:

1. A liquid drug medical device for use with a source of physiological solution and a medicinal vessel for administration of a liquid drug, the device having a longitudinal axis, and comprising:
    (a) a body member having a first port for fluid connection with the source of physiological solution, said first port being co-directional with the longitudinal axis;
    (b) a flow control member rotatably mounted in said body member about an axis of rotation, and having a first major flow duct and a second major flow duct respectively terminating at a second port, and a third port for administering the liquid drug; and
    (c) a manually rotatable vial adapter for receiving the medicinal vessel, the manually rotatable vial adapter having a fluid conduit member with a proximal end in flow communication with said second port and a distal end adapted to extend into the medicinal vessel on its attachment to said vial adapter, and coupled to said flow control member for rotating the flow control member between a first flow control position which connects said first port with said second port, and a second flow control position which connects said first port with said third port,
    said axis of rotation is co-directional with the longitudinal axis, and said first major flow duct and said second major flow duct are both substantially parallel to and non-coaxial with said axis of rotation and wherein said distal end of the fluid conduit member extends into a recess in the vial adapter.

2. The device according to claim 1 wherein said vial adapter is detachable from said body member at said second flow control position along a line of detachment co-directional with the longitudinal axis.

3. The device according to claim 2 wherein said first port has a screw thread for screw threadingly receiving the source of physiological solution in one direction and said adaptor screw threadingly detaches from said body member in an opposite direction.

4. The device according to claim 3 wherein the device is packaged in a sterile packaging and said body member has at least one laterally protruding member for stopping against an internal longitudinally directed stopper on the inside of the sterile packaging on screw threading the source of physiological solution into said first port whereupon said flow control member is urged into said first flow control position.

5. The device according to claim 4 wherein said vial adapter has a stem including said fluid conduit member and a bore parallel thereto and co-extensive therewith for accommodating a drug dispenser coupled to said third port.

6. The device according to claim 5 wherein said third port is fitted with a needle stick.

7. The device according to claim 5 wherein said third port is fitted with an atomizer.

* * * * *